(12) United States Patent
Sroka

(10) Patent No.: US 8,495,931 B2
(45) Date of Patent: Jul. 30, 2013

(54) RATCHET WRENCH

(76) Inventor: John S. Sroka, Richfield, OH (US)

( * ) Notice: Subject to any disclaimer, the term of this patent is extended or adjusted under 35 U.S.C. 154(b) by 482 days.

(21) Appl. No.: 12/766,559

(22) Filed: Apr. 23, 2010

(65) Prior Publication Data
US 2010/0269639 A1 Oct. 28, 2010

Related U.S. Application Data

(60) Provisional application No. 61/172,020, filed on Apr. 23, 2009.

(51) Int. Cl.
*B25B 13/46* (2006.01)
*B25B 13/08* (2006.01)
*B25B 13/58* (2006.01)

(52) U.S. Cl.
USPC .................. 81/58.2; 81/185.1; 81/62

(58) Field of Classification Search
USPC ..................... 81/58.2, 62, 185.1, 60
See application file for complete search history.

(56) References Cited

U.S. PATENT DOCUMENTS

| | | | | |
|---|---|---|---|---|
| 1,060,185 A | * | 4/1913 | Hitt | ............................... 81/58.2 |
| 2,353,901 A | * | 7/1944 | Jires | ................... 81/62 |
| 2,851,914 A | * | 9/1958 | Zeckzer | ..................... 81/58.2 |
| 5,388,479 A | | 2/1995 | Sroka | |
| 5,501,124 A | | 3/1996 | Ashby | |
| D423,891 S | | 5/2000 | Melvin et al. | |
| 6,460,431 B1 | * | 10/2002 | Chen | ............................... 81/63.2 |
| D584,932 S | | 1/2009 | Chang et al. | |
| D596,002 S | | 7/2009 | Bunker | |
| 2002/0026858 A1 | | 3/2002 | Hu | |
| 2006/0137492 A1 | * | 6/2006 | Melos | ........................... 81/58.2 |

FOREIGN PATENT DOCUMENTS

| | | |
|---|---|---|
| EP | 2 135 708 A1 | 12/2009 |
| JP | 3109108 U | 3/2005 |

OTHER PUBLICATIONS

International Search Report for PCT/US2010/032252 dated Jan. 28, 2011.

* cited by examiner

*Primary Examiner* — Hadi Shakeri
(74) *Attorney, Agent, or Firm* — Pearne & Gordon LLP

(57) ABSTRACT

A ratchet wrench is provided comprising a wrench handle with a head. A ratchet member has a plurality of ratchet teeth and is seated in the head for rotation about an axis. A pawl disposed within the head is adapted to pivot relative to the ratchet member. The pawl is provided with first and second pluralities of pawl teeth disposed for movement into and out of engagement with the ratchet teeth. A selector mechanism selectively pivots the pawl to move a selected one of the first and second pluralities of pawl teeth into engagement with the ratchet teeth. In one example, the selector mechanism can selectively permit the ratchet member to perform at least three functions.

13 Claims, 10 Drawing Sheets

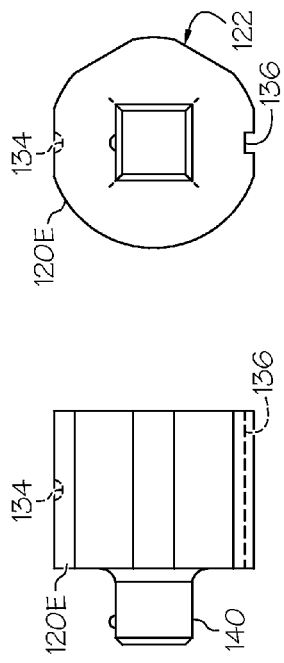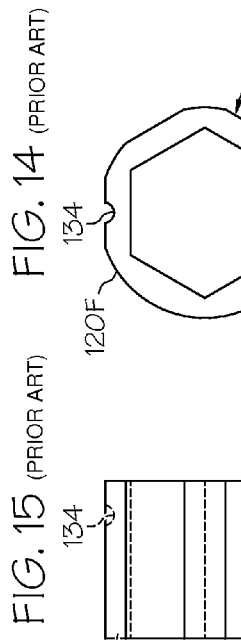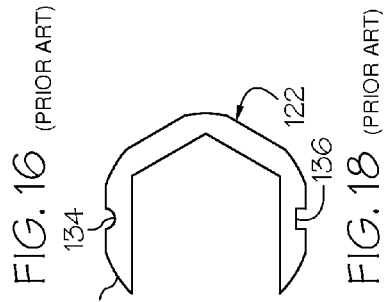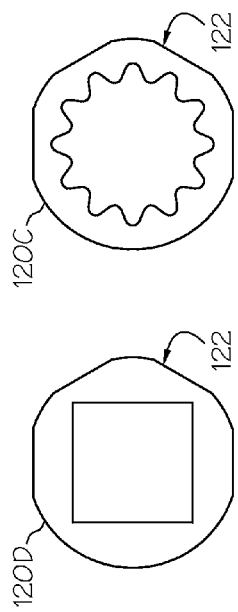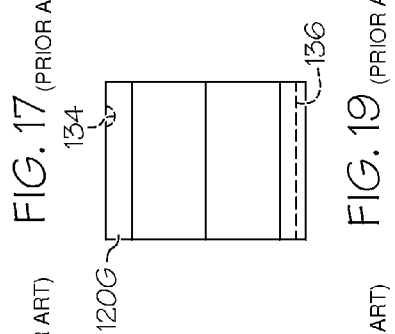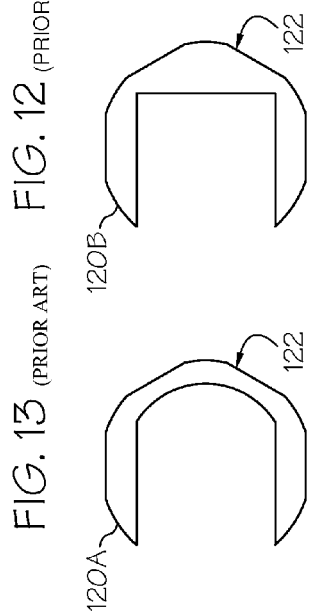

RATCHET WRENCH

INCORPORATION BY REFERENCE

This application claims the benefit of U.S. Provisional Application No. 61/172,020, filed Apr. 23, 2009, the entire disclosure of which is hereby incorporated herein by reference.

FIELD OF THE INVENTION

The present invention relates generally to a ratchet wrench for tightening or loosening nuts, bolts, fasteners, and the like.

BACKGROUND OF THE INVENTION

Ratchet wrenches are well known. Most ratchet wrenches utilize a socket, where the socket includes an opening formed in the shape of a specific fastener size, for example, a half inch hexagonal bolt or a 14 mm twelve point bolt head. Most ratchet wrenches are sold with a variety of sockets, each socket designed to fit a specific sized bolt or nut.

In such wrenches, the wrench includes structure adapted to secure the socket to a ratchet mechanism such that a variety of sockets may be interchangeably attached to the wrench. In recent years, ratchet wrenches and sockets have been standardized where the ratchet wrench includes a protruding shank that is ⅜ inch square and the socket has a ⅜ inch square opening to accommodate the shank. Another standard size ratchet wrench shank is ½ inch square with the sockets having corresponding ½ inch square openings.

Typically, a ratchet wrench selectively allows the socket to rotate freely in one direction, but inhibits rotation in the reverse direction so that as a bolt is tightened or loosened, the wrench does not need to be removed from the bolt. Open end wrenches have been used for over a century. Open end wrenches typically have a U-shaped opening at one end with opposed parallel faces that are manufactured to fit one single bolt or nut size. Open end wrenches allow a technician or handyman to engage a bolt or nut when only a radial face of the bolt or nut is exposed. A drawback to an open end wrench is that the user must constantly remove the wrench from the bolt or nut and reposition the wrench in order to tighten or loosen the bolt or nut.

BRIEF SUMMARY OF THE INVENTION

The following presents a simplified summary of the invention in order to provide a basic understanding of some example aspects of the invention. This summary is not an extensive overview of the invention. Moreover, this summary is not intended to identify critical elements of the invention nor delineate the scope of the invention. The sole purpose of the summary is to present some concepts of the invention in simplified form as a prelude to the more detailed description that is presented later.

In accordance with one aspect of the present invention, a ratchet wrench is provided, comprising a wrench handle having a head formed with an open end. The open end defines an axis that extends therethrough, and the head has a recess formed on an inner surface thereof. A ratchet member is seated in the recess for rotation about the axis, comprising a radially extending outer surface that is generally parallel to the axis. The surface is provided with a plurality of ratchet teeth. A pawl is disposed within an aperture of the recess and is adapted to pivot relative to an orientation pin. The pawl is provided with a first plurality of pawl teeth spaced a distance from a second plurality of pawl teeth, and the first and second pluralities of pawl teeth are disposed for movement into and out of engagement with the ratchet teeth. A selector mechanism is provided for selectively pivoting the pawl to move a selected one of the first and second pluralities of pawl teeth into engagement with the ratchet teeth. The selector mechanism is at least partially disposed within the wrench.

In accordance with another aspect of the present invention, a ratchet wrench is provided, comprising a wrench handle having a head formed with an open end. The open end defines an axis that extends therethrough, and the head has a recess formed on an inner surface thereof. A ratchet member is seated in the recess for rotation about the axis, and comprises a radially extending outer surface that is generally parallel to the axis. The surface is provided with a plurality of ratchet teeth that extend along a predetermined radial distance of the surface. First and second pawls are each disposed within respective apertures of the recess and adapted to pivot relative thereto. Each of the first and second pawls are provided pawl teeth disposed for selective movement into and out of engagement with the ratchet teeth. The plurality of ratchet teeth extend along a predetermined radial distance of the surface of the ratchet member such that the ratchet member is permitted to rotate completely about the axis with at least a portion of the ratchet teeth always in contact with pawl teeth of at least one of the first and second pawls.

In accordance with another aspect of the present invention, a ratchet wrench is provided, comprising a wrench handle having a head formed with an open end. The open end defines an axis that extends therethrough, and the head has a recess formed on an inner surface thereof. A ratchet member is seated in the recess for rotation about the axis, comprising a radially extending outer surface that is generally parallel to the axis. The surface is provided with a plurality of ratchet teeth that extend along a predetermined radial distance of the surface. First and second pawls are each disposed within respective apertures of the recess and are adapted to pivot relative thereto. Each of the first and second pawls are provided pawl teeth disposed for movement into and out of engagement with the ratchet teeth. A selector mechanism is provided for selectively and independently pivoting the first and second pawls to into and out of engagement with the ratchet member to selectively permit the ratchet member to perform at least three functions.

It is to be understood that both the foregoing general description and the following detailed description present example and explanatory embodiments of the invention, and are intended to provide an overview or framework for understanding the nature and character of the invention as it is claimed. The accompanying drawings are included to provide a further understanding of the invention and are incorporated into and constitute a part of this specification. The drawings illustrate various example embodiments of the invention, and together with the description, serve to explain the principles and operations of the invention.

BRIEF DESCRIPTION OF THE DRAWINGS

The foregoing and other aspects of the present invention will become apparent to those skilled in the art to which the present invention relates upon reading the following description with reference to the accompanying drawings, in which:

FIGS. 10-19 show a variety of example inserts that can be inserted into the ratchet member of the ratchet wrench.

DESCRIPTION OF EXAMPLE EMBODIMENTS

Figure 1:
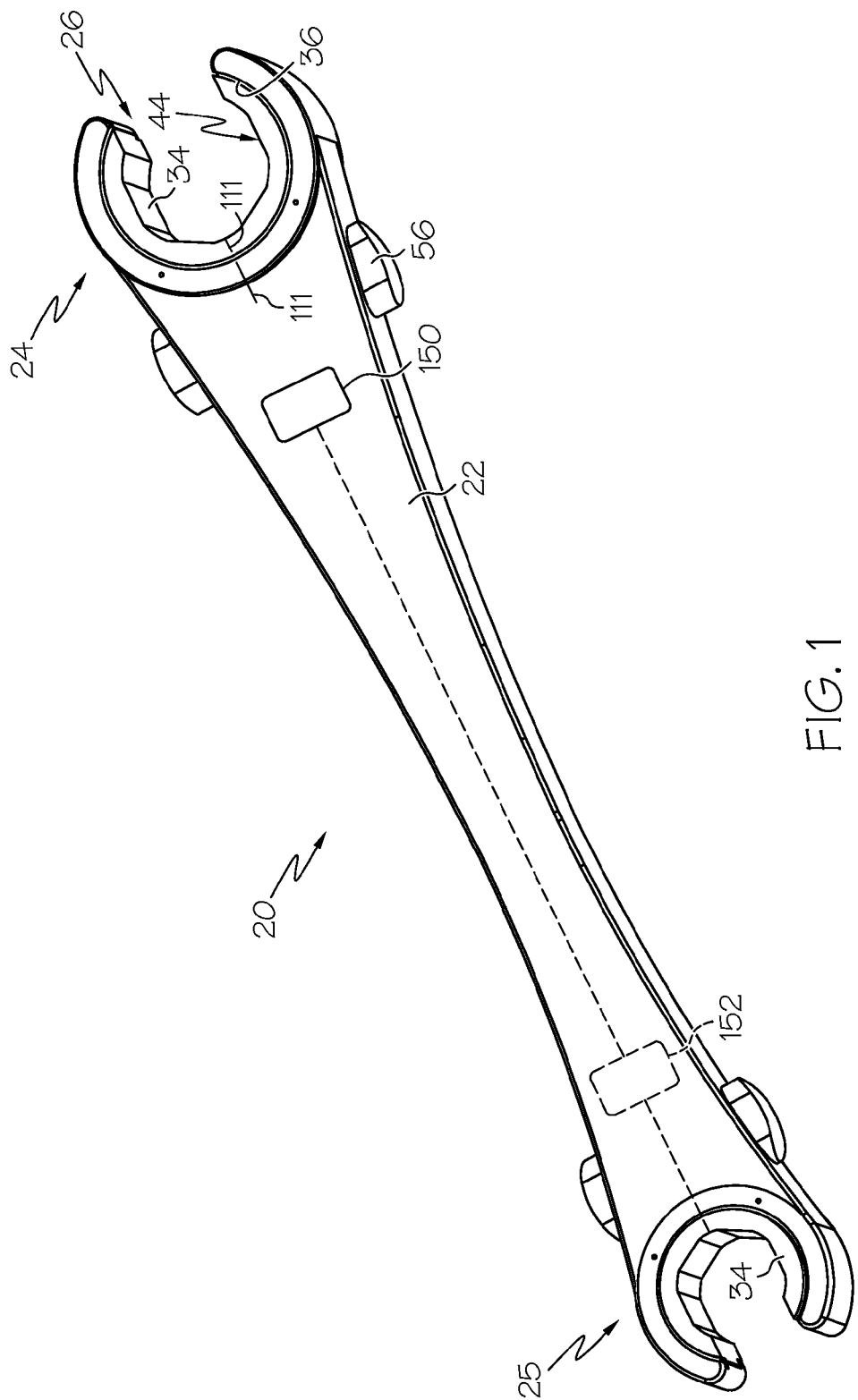
FIG. 1 is a perspective of an example ratchet wrench.

Example embodiments that incorporate one or more aspects of the present invention are described and illustrated in the drawings. These illustrated examples are not intended to be a limitation on the present invention. For example, one or more aspects of the present invention can be utilized in other embodiments and even other types of devices. Moreover, certain terminology is used herein for convenience only and is not to be taken as a limitation on the present invention. Still further, in the drawings, the same reference numerals are employed for designating the same elements.

Turning to the example shown in the FIG. 1, an example ratchet wrench 20 is provided. The ratchet wrench 20 can generally include a handle 22 having at least one head 24 formed at an end of the handle 22. In the shown examples, the handle 22 can include at least two heads 24, 25 disposed on opposite ends of the handle. It should be understood, however, that the handle 22 can be an elongated member that extends well beyond the depiction shown in the various Figures, as is well known in the art. For clarity, the wrench 20 will be discussed with reference to the one head 24, though it is understood that such description can similarly apply to other head(s) 25. In another example, the wrench 20 may only include a head at one end, and gripping structure or the like at the other end. In various examples, each head 24 can be provided with similar or different structure and/or functions that include, but are not limited to: an open end; a closed end; a fixed aperture sized for interacting with a fixed-size fastener; a rotatable, ratcheting aperture sized for interacting with a fixed-size fastener; a fixed aperture sized for interacting with an interchangeable insert for different-size fasteners; and/or a rotatable, ratcheting aperture sized for interacting with an interchangeable insert for different-size fasteners. It is understood that the various sectional views in the Figures are taken generally centrally along the head 24 end of the wrench 20.

In the shown example, the head 24 is formed with a gap 26 that defines the open end. The head 24 is also formed with a recess 28 on an inner surface thereof that provides a side wall 27 having generally cylindrical contour. The cylindrical contour of the side wall 27 is formed about an axis 30 that extends generally through the center of the head 24. The head 24 is formed with a radially extending flange 32 that has an upper surface that forms the bottom of the recess 28. The upper surface of the flange 32 is generally planar and is perpendicular to the axis 30. The flange 32 further defines a flange sidewall 33 that has a diameter relatively less than the side wall 27 of the recess 28. The flange sidewall 33 can extend radially around the full extent of the recess 28, and be machined to a relatively tight tolerance, such as to about 0.001 inches or other value.

In addition or alternatively, any of the head(s) 24 can be arranged at an angle and/or offset relative to the handle 22. In one example, not shown, a head 24 can be arranged at an angle of approximately 15 degrees relative to the longitudinal axis of the handle 22. In another example, not shown, a portion of the handle 22 can be bent such that the head 24 is vertically offset a distance from the handle 22.

In addition or alternatively, the wrench 20 can include torque sensing structure operatively coupled to the ratchet member 34 for indicating (i.e., visual, audible, tactile, etc.) and/or controlling an amount of torque that can be applied by the wrench 20, such as structure found on a torque wrench or the like. In one example, the torque sensing structure 152 (see FIG. 1) can operate to limit a maximum amount of torque that can be applied by the wrench 20. The torque sensing structure 152 can include a mechanical or electronic clutch or the like that can inhibit, such as prevent, the wrench 20 from applying torque greater than a predetermined or user-definable limit. For example, the torque sensing structure 152 can be applied to one or more heads of the wrench, and can include mechanical, electrical, analog and/or digital structure, displays, sound, etc. In one example, the torque sensing structure 152 can be operatively coupled to a mechanical or electronic display 150 to display the actual, sensed torque applied by the wrench 20. The display 150 can maximum and/or minimum readings, predetermined or user-definable alarm limits, etc.

As described herein, any head 24 of the wrench 20 can include ratcheting structure that enables at least a portion of the head 24, such as a ratchet member 34, to rotate relative to the handle 22. The ratcheting structure can enable the ratchet member 34 to perform at least one function, at least two functions, at least three functions, at least four functions, or even more functions. In one example, the ratcheting structure can be configured to allow the ratchet member 34 to rotate in one direction only, such as clockwise (i.e., "CW" function) or counter-clockwise (i.e., "CCW" function), while inhibiting rotation in the opposite direction. In another example, the ratcheting structure can be configured to allow the ratchet member 34 to rotate in both directions CW and CCW (i.e., "neutral" function). In yet another example, the ratcheting structure can be configured to inhibit the ratchet member 34 from rotating in either direction (i.e., "lock" or "stationary" function).

For example, rotatable within the head 24 and about the axis 30 is the ratchet member 34. The ratchet member 34 can be located within the head recess 28 and can be seated upon the flange 32. The ratchet member 34 can be removably retained within the head recess 28 in various manners, such as by a spring clip 36 seated in an annular groove 38, fasteners, or the like. In another example, the ratchet member 34 can also be non-removable. The ratchet member 34 is generally circular in shape, but can be formed with a gap 40 that conforms generally to and can be aligned with the gap 26 in the open end of the head 24 and provides a generally C-shaped geometry. The gap 40 of the ratchet member 34 may be smaller, the same, or even larger than the gap 26 of the head 24. In other examples, the ratchet member 34 may be continuous and not include a gap. It can be beneficial for the width of the gap 26 of the head 24 to be sized relatively less than the outer diameter of the ratchet member 34. For example, the width of the gap 26 can be sized relative to the outer diameter of the ratchet member 34, such as at a ratio of 1:4, 1:5, or 1:6, though other ratios are also contemplated. These ratios can inhibit, such as prevent, the ratchet member 34 from being inadvertently removed from the recess 28 of the head 24 via the gap 26.

Figure 6:
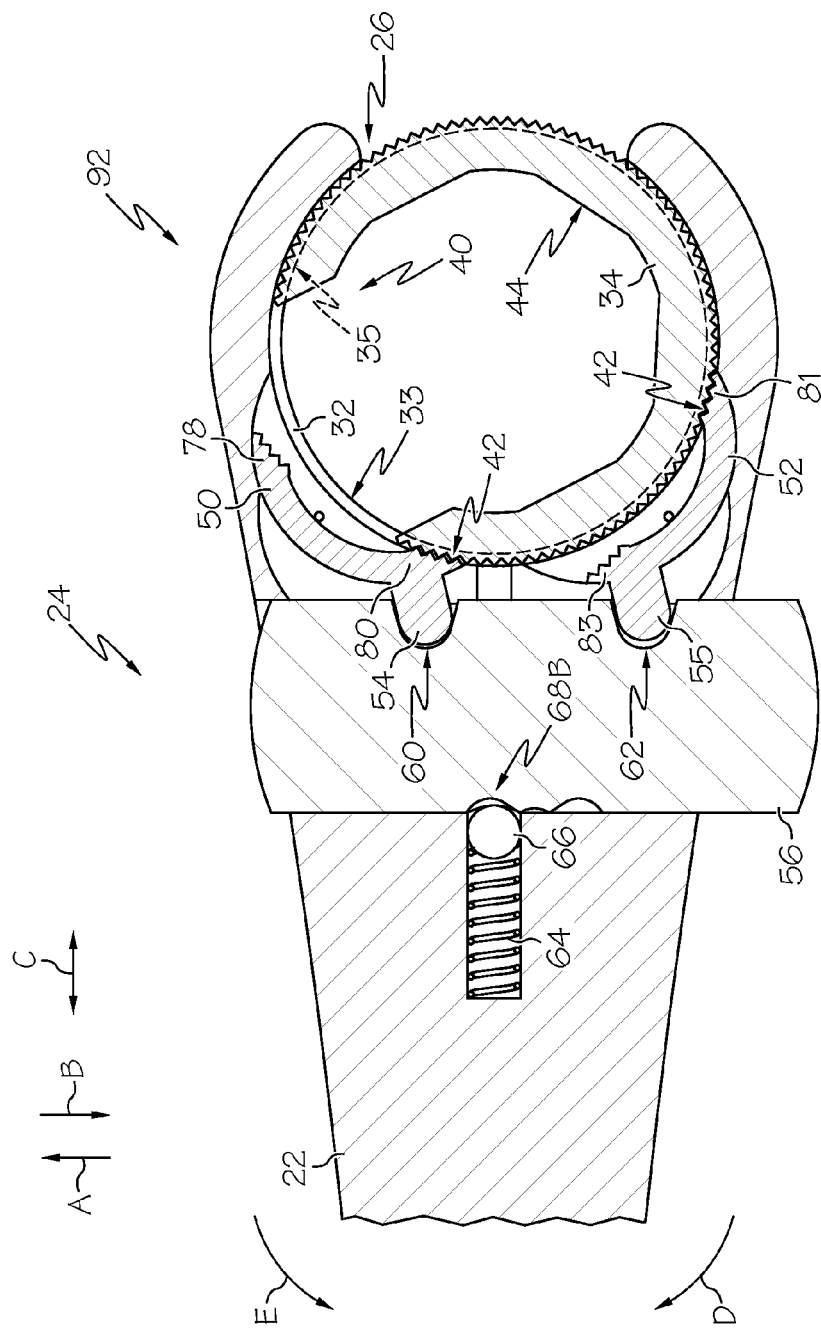
FIG. 6 is similar to FIG. 5, but shows an example ratchet member in a different orientation.

The ratchet member 34 can further include a radially extending outer surface that is generally parallel to the axis 30, and can have a geometry generally conforming to the side wall 27 of the recess 28. The ratchet member 34 is provided with an inner surface 44 adapted to be functionally useful as a wrench, and/or can be also adapted to retain any of a variety of wrench inserts as will be described herein. The outer surface can be provided with a plurality of ratchet teeth 42. For example, at least a portion of the outer surface can be provided with the ratchet teeth 42, such as where the ratchet teeth 42 are disposed along substantially all of the radial extent of the surface. The ratchet teeth 42 can extend vertically along at least a portion of the height of the outer surface, though may not extend along the full height of the outer surface. For example, as shown in FIG. 6, the ratchet teeth 42 can be generally centrally located on the outer surface of the ratchet member. A lower portion of the ratchet member 34, located adjacent the flange 32 of the recess 28, can define an inset radial bore 35 having a relatively smaller diameter than the portion of the ratchet member with the teeth 42. The inset radial bore 35 can extend generally around the entire radial length of the ratchet member 34 (see FIG. 6) and can be adapted to abut and slide against the flange sidewall 33 of the recess 28. The inset radial bore 35 can have a corresponding geometry to that of the flange 32 and flange sidewall 33, and can be similarly machined smooth to a relatively tight tolerance, such as to about 0.001 inches or other value. Due to the relatively tight tolerances of the flange sidewall 33 and the inset radial bore 35, smooth rotation of the ratchet member 34 can be achieved in various orientations of the wrench 22 and/or low-torque or high-torque applications. Similarly, the relatively tight tolerances of the flange sidewall 33 and the inset radial bore 35 can inhibit, such as prevent, the ratchet member 34 from pivoting off-axis, binding, etc. to maintain a rotational axis of the ratchet member 34 to be generally coaxial with the axis 30. Further, the relatively tight tolerances can provide protection from damage (e.g., protecting the ratchet teeth 42), retain lubricants, and/or resistance to outside debris, etc.

At least two dual acting pawls 50, 52 can allow for any of the described functions, such as continuous ratcheting in either direction (i.e., CW or CCW functions) of the ratchet member 34 around the inside of the recess 28 of the head 24. In other examples, the at least two pawls 50, 52 can allow for the neutral and/or lock functions. The dual acting pawls 50, 52 can be independently operable, but can operate in synchronization and may be positioned for left, right, neutral and stationary engagement to permit clockwise, counter-clockwise, or neutral rotation of the ratchet member 34, or a stationary locked condition. Though the example pawls 50, 52 are illustrated disposed generally towards the handle portion, it is to be understood that the pawls 50, 52 can be disposed at various locations about the head 24 of the wrench 20. Additionally, more than two pawls can be utilized. For clarity, the wrench 20 will be discussed with reference to the one pawl 50, though it is understood that such description can similarly apply to other pawl(s) 52.

The wrench 20 can further include a selector mechanism for selectively and independently pivoting the first and second pawls 50, 52 to into and out of engagement with the ratchet member 34 to selectively permit the ratchet member 34 to perform at least three functions. For example, the selector mechanism can selectively pivot the pawl 50 to move a selected one of a first and second pluralities of pawl teeth into engagement with the ratchet teeth 42. In one example, the wrench 20 can include a selector cam 56. The selector cam 56 can synchronize the operation of the dual acting pawls 50, 52.

In addition, an orientation pin 58 can be disposed generally in the middle of each pawl 50, such as in a curved valley, to facilitate maintaining orientation of the pawl 50 relative to the head 24 of the wrench 20. For example, the pawl 50 can move, such as pivot, about the orientation pin 58. The pin 58 can be press-fit into the head 24, or retained in various other manners. The pin 58 may or may not be load bearing.

Each pawl 50 can include a tongue 54 for engagement with the selector cam 56 for moving, such as pivoting, the pawl 50. The tongue 54 can be disposed variously on the pawl 50, such as centrally located on the pawl 50, offset from the pawl 50, etc. As shown, the tongue 54 can be disposed towards one end of the pawl 50, and can be vertically centered thereon. The selector mechanism can be at least partially disposed within the wrench 20. For example, a majority of the selector cam 56 can be disposed within the wrench 20, though portions can extend from the sides and/or even through the top to permit a user to actuate the selector cam 56. In another example, not shown, the selector cam can include a rotatable member that extends vertically through the wrench 20, with a rotatable cam for selectively toggling the pawls 50, 52.

Figure 4:
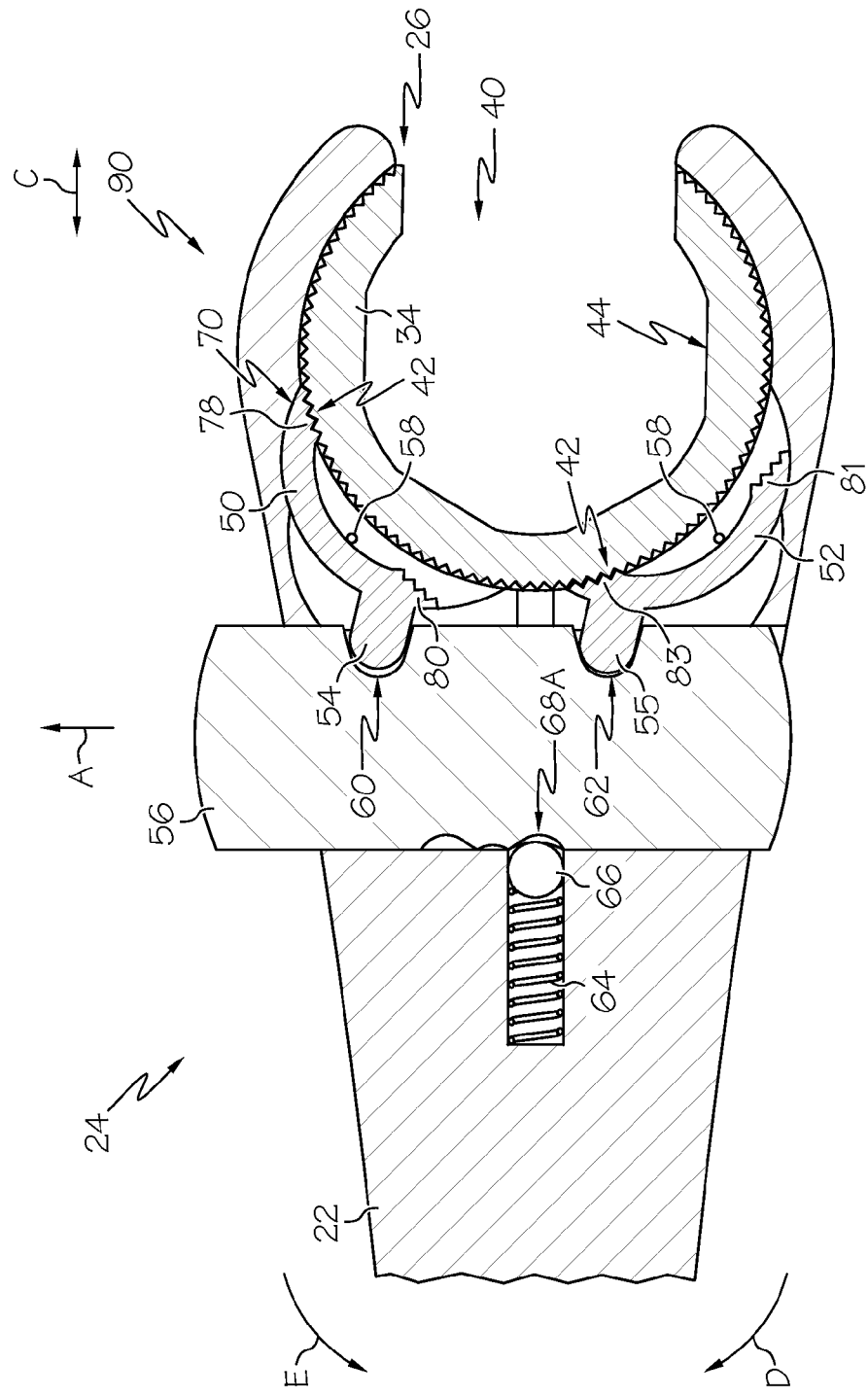
FIG. 4 is similar to FIG. 3, but shows another function of the ratchet wrench.
Figure 5:
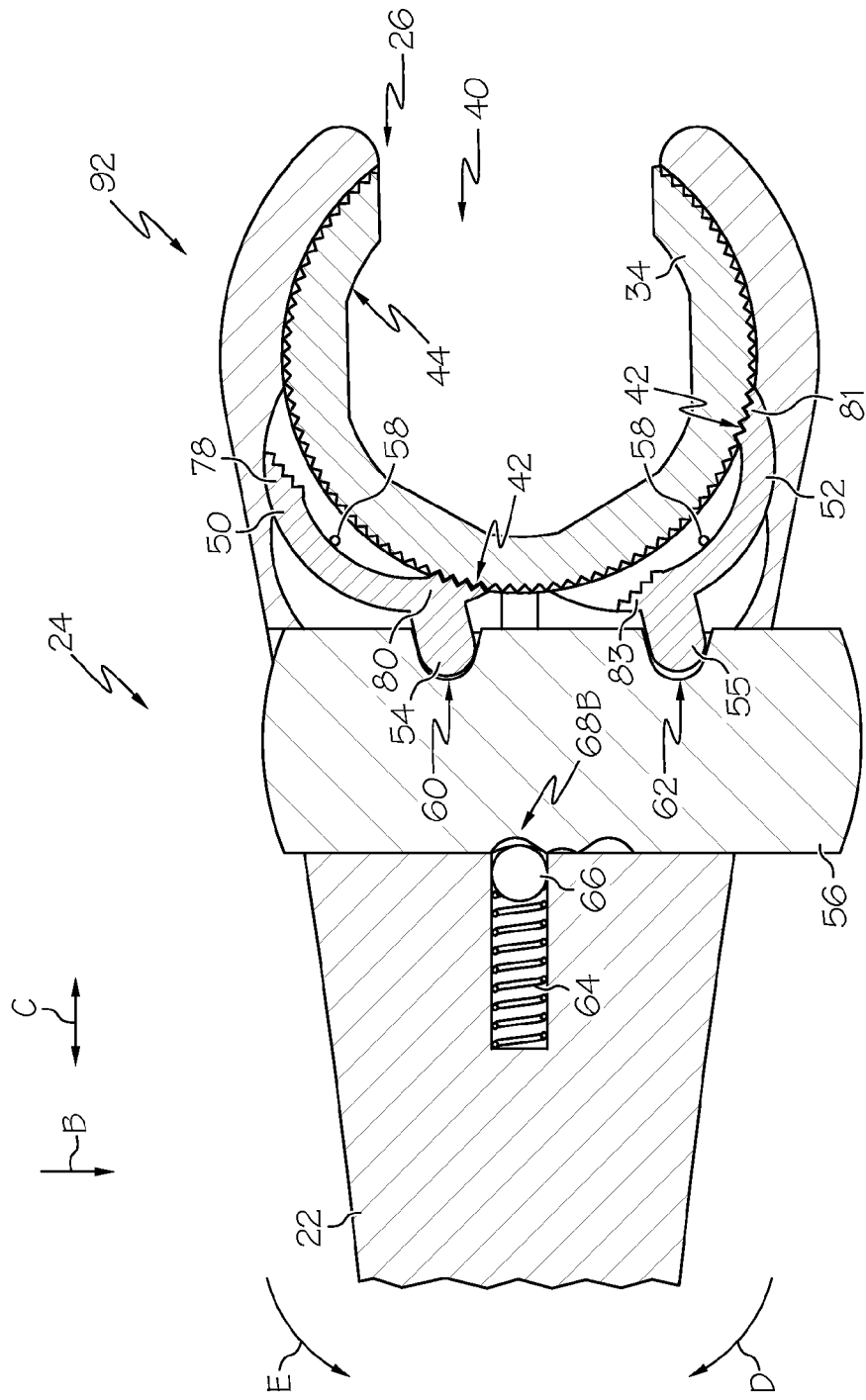
FIG. 5 is similar to FIG. 3, but shows yet another function of the ratchet wrench.

The selector cam 56 can be linearly slidable, rotatable, etc. In the shown example, the selector cam 56 can be disposed in an aperture 21 extending through the head 24 of the wrench 20, and can be linearly slidable therein among various positions, such as along the direction of arrows A and B. As shown, an end portion of the selector cam 56 can extend a distance from the head 24 of the wrench 20, and can be slidably movable by pressing against said end portion in the desired direction of movement. Where two pawls 50, 52 are used, each pawl can include a tongue 54, 55 engaged with the selector cam 56. For example, the selector cam 56 can include a recess for receiving each tongue, such as a first recess 60 for receiving the tongue 54 of the first pawl 50 and a second recess 62 for receiving the tongue 55 of the second pawl 52. The first and second recesses 60, 62 can have a rounded, concave geometry that corresponds to the rounded, convex geometry of the tongues 54, 55 to permit relative rotation thereof. For example, sliding movement of the selector cam can cause similar, pivoting movement of each pawl 50, 52. For example, as shown in FIG. 4, sliding movement of the selector cam 56 along the direction of arrow A causes both of the pawls 50, 52, via interaction between the tongues 54, 55 and the recesses 60, 62, to pivot about the respective orientation pins 58 in the direction of arrow D. Similarly, as shown in FIG. 5, sliding movement of the selector cam 56 along the direction of arrow B causes both of the pawls 50, 52, via interaction between the tongues 54, 55 and the recesses 60, 62, to pivot about the respective orientation pins 58 in the direction of arrow E.

In addition or alternatively, one or more compression springs or spring clips can be coupled to and/or located within the selector cam 56 to provide a ratcheting action through the pawl tongue 54. For example, the selector cam 56 can be held in a desired position by a compression spring 64 and ball 66 resiliently pushing against cam position grooves 68 (e.g., detents) on a back-side of the selector cam 56. In another example, the compression spring 64 and ball 66 can be carried by the selector cam 56 for engagement with cam position grooves in the body of the handle 22. The selector cam 56 may be permitted to move slightly forward and backward, along the directions of arrow C, in response to the pivoting ratcheting movement of the pawls 50, 52 relative to the head 24 of the handle to provide the ratcheting action. To facilitate this forward and backward action of the selector cam 56, some of the cam position grooves 68 can be oversized. In another example, not shown, compression springs can be disposed between the tongue 54 and recess 60 to provide the ratcheting action.

Figure 2:
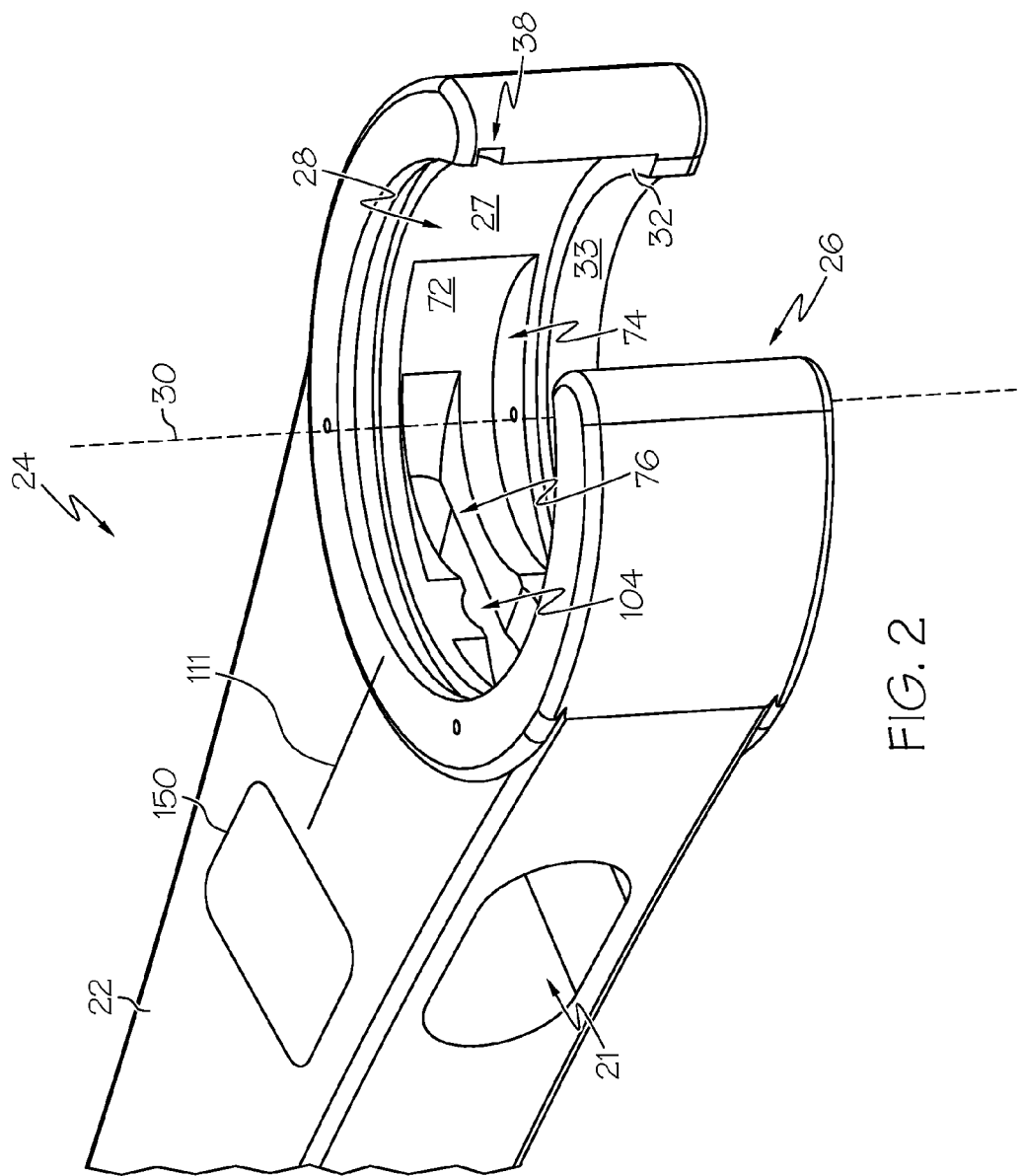
FIG. 2 is partial, detail perspective view of a head of the ratchet wrench of FIG. 1.

Each dual-acting pawl 50 can include a generally curved outer surface 70 that rides against a correspondingly curved inner wall 72 of the head 24. For example, as shown in FIG. 2, the recess 28 of the head 24 can include an aperture 74 having the curved inner wall 72 that the pawl 50 rides against. The curved inner wall 72 can be sized to permit desired pivoting of the pawl 50 about the orientation pin 58. Additionally, the aperture 74 can also include a secondary aperture 76 adapted to receive the tongue 54 of the pawl 50 for interaction with the selector cam 56. It is understood that each of the first and second pawls 50, 52 are each disposed within respective apertures of the recess 28 and are adapted to pivot relative thereto. Thus, the pawls 50, 52 can be positioned at least partially, such as completely, within the head 24 of the wrench 20 to provide protection from damage (e.g., protecting the pawl teeth), retain lubricants, and/or resistance to outside debris, etc. Indeed, it is understood that the overall design of the wrench 20 has been simplified to utilize a reduced number of parts to facilitate maintenance and operability in various environments, even in harsh commercial and/or military environments.

Each dual-acting pawl 50, 52 can also include a first plurality of pawl teeth 78 spaced a distance from a second plurality of pawl teeth 80. For example, the first and second pluralities of pawl teeth 78, 80 can be separated by a curved, toothless valley that rides near or against the orientation pin 58. The first and second pluralities of pawl teeth 78, 80 can be adapted to engage with the ratchet teeth 42 extending along the outer surface of the ratchet member 34. That is, the first and second pluralities of pawl teeth 78, 80 are disposed for movement into and out of engagement with the ratchet teeth 42. As shown in FIGS. 4 and 5, due to the pivoting action of the pawl 50 about the orientation pin 58, a selected one of the first and second pluralities of pawl teeth 78, 80 will be engaged with the ratchet teeth 42, while the other of the first and second pluralities of pawl teeth 78, 80 is disengaged from the ratchet teeth 42.

Additionally, the wrench 20 is adapted to permit the ratchet member 34 to completely and continuously rotate a full 360 degrees about the axis 30. The plurality of ratchet teeth 42 extend along a predetermined radial distance of the surface of the ratchet member 34 such that the ratchet member 34 is permitted to rotate completely about the axis 30 with at least a portion of the ratchet teeth 42 always in contact with pawl teeth of at least one of the first and second pawls 50, 52. For example, the pawls 50, 52 can be sized and/or positioned within the head 24, taking into account the width of the gap 40 of the ratchet member 34, such that at least some of the pawl teeth 78, 80, 81, 83 of at least one of the pawls 50, 52 is always in contact with the ratchet teeth 42 of the ratchet member 34. As a result, the ratcheting action is available in any orientation of the wrench 20. For example, as shown in FIG. 6, the ratchet member 34 has been rotated, relative to the handle 22, along the direction of arrow E. The ratchet teeth 42 are in ratcheting engagement with the pawl teeth 80 of pawl 50 and pawl teeth 81 of pawl 52. If the ratchet member 34 continues to be rotated along the direction of arrow E, the gap 40 will cause the pawl teeth 80 of pawl 50 will not be engaged with the ratchet teeth 42. However, the pawl teeth 81 of pawl 52 will still be engaged with the ratchet teeth 42 to provide the continuous ratcheting action until the pawl teeth 80 of pawl 50 can again engage the ratchet teeth 42 after the gap 40.

As discussed above, the ratchet member 34 can perform at least three functions by movement of the selector cam 56 to each of a first, second, or third position. One example function, shown in FIG. 4, occurs when the selector cam 56 is shifted to a first position 90 along the direction of arrow A. The ball 66 is moved into a first cam position groove 68A on a back-side of selector cam 56 to maintain the selector cam 56 in the first position 90. Each of the pawls 50, 52 is caused to pivot about the orientation pins 58 along the direction of arrow D such that at least one of the respective pluralities of teeth 78, 83 of the pawls 50, 52 engage the ratchet teeth 42 of the ratchet member 34. The other pluralities of teeth 80, 81 of each pawl 50, 52 remain disengaged from the ratchet teeth 42. Thus, when the wrench handle 22 is also rotated in the direction of arrow D, the reactionary force of the ratchet teeth 42 acting on the pawl teeth 78 causes the pawl 50 to move slightly towards the left against the selector cam 56. The selector cam 56 can similarly move, against the force of the spring 64, to thereby permit free ratcheting rotation of the ratchet member 34 in direction of arrow D. That is, the wrench 20 can be freely rotated in the direction of arrow D while the ratchet member 34 remains relatively stationary. It is understood that although selector cam 56 appears to be tightly fit into the handle 22, the selector cam 56 is able to move (e.g., left and right in FIG. 4) a sufficient amount to enable the free ratcheting rotation of the ratchet member 34 against the pawl 50. Alternatively, when the wrench handle 22 is rotated oppositely, in the direction of arrow E, the reactionary force of the ratchet teeth 42 acting on the pawl teeth 78 causes the pawl 50 to be trapped and/or move slightly towards the right to thereby cause impinging or binding engagement between the generally curved outer surface 70 of the pawl 50 against the correspondingly curved inner wall 72 of the head 24. The impinging or binding engagement can occur along any portion of the outer surface 70 of the pawl 50, such as portions near the either or both of the pluralities of teeth 78, 83. The impinging or binding engagement inhibits, such as prevents, relative rotational movement of the ratchet member 34. That is, the wrench handle 22 can be rotated in the direction of arrow E only together with the ratchet member 34, such as to tighten a bolt or the like.

Similarly, the reverse situation can also apply. Another example function, shown in FIG. 5, occurs when the selector cam 56 is shifted to a second position 92 along the direction of arrow B. The ball 66 is moved into a second cam position groove 68B on a back-side of selector cam 56 to maintain the selector cam 56 in the second position 92. Each of the pawls 50, 52 is caused to pivot oppositely about the orientation pins 58 along the direction of arrow E such that at least one of the respective pluralities of teeth 80, 81 of the pawls 50, 52 engage the ratchet teeth 42 of the ratchet member 34. The other pluralities of teeth 78, 83 of each pawl 50, 52 now are released and remain dis-engaged from the ratchet teeth 42. Thus, when the wrench handle 22 is also rotated in the direction of arrow E, the reactionary force of the ratchet teeth 42 acting on the pawl teeth 81 causes the pawl 52 to move slightly towards the left against the selector cam 56. As before, the selector cam 56 can similarly move, against the force of the spring 64, to thereby permit free ratcheting rotation of the ratchet member 34 in direction of arrow E. That is, the wrench 20 can be freely rotated in the direction of arrow E while the ratchet member 34 remains relatively stationary. Alternatively, when the wrench handle 22 is rotated oppositely, in the direction of arrow D, the reactionary force of the ratchet teeth 42 acting on the pawl teeth 81 causes the pawl 52 to be trapped and/or move slightly towards the right to thereby cause impinging or binding engagement between the generally curved outer surface 70 of the pawl 52 against the correspondingly curved inner wall 72 of the head 24. The impinging or binding engagement can occur along any portion of the outer surface 70 of the pawl 50, such as portions near the either or both of the pluralities of teeth 80, 81. The impinging or binding engagement inhibits, such as prevents, relative rotational movement of the ratchet member 34. That is, the wrench handle 22 can be rotated in the direction of arrow D only together with the ratchet member 34, such as to tighten a bolt or the like. It is understood that the rotational directions along the directions of arrows D and E can correspond to either of the rotational clockwise and counter-clockwise directions, depending upon the orientation of the wrench 20.

Figure 3:
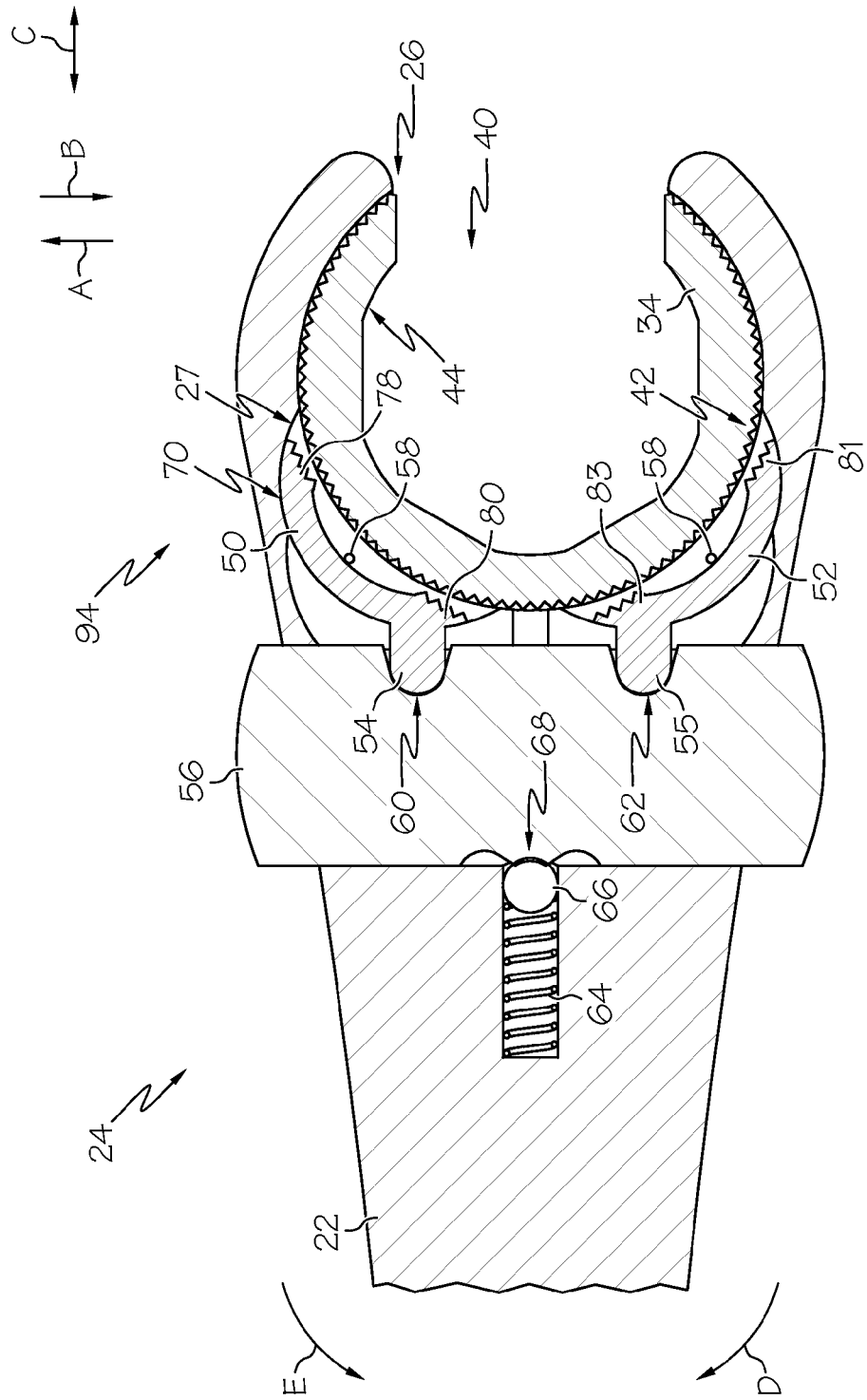
FIG. 3 is a partial sectional view of the ratchet wrench of FIG. 1 showing a function of the ratchet wrench.

Yet another example function, shown in FIG. 3, occurs when the selector cam 56 is shifted to a third position 94, which can be a neutral position located generally between the first and second positions 90, 92. The ball 66 is moved into the main cam position groove 68 on a back-side of selector cam 56 to maintain the selector cam 56 in the third position 94. Each of the pawls 50, 52 is pivoted to neutral positions such that none of the respective pluralities of pawl teeth 78, 80, 81, 83 are in engagement with the ratchet teeth 42 of the ratchet member 34, and no ratcheting action occurs. As a result, the pawls 50, 52 are separated from the ratchet member 34 such that the ratchet member can freely rotate within the recess 28 of the head 24. Thus, the ratchet member 34 is able to freely rotate in either of the directions of arrows D and E independent of handle 22 movement. Still, it is also contemplated that some structure can be provided to enable tactile feedback during rotation of the ratchet member 34.

Figure 7:
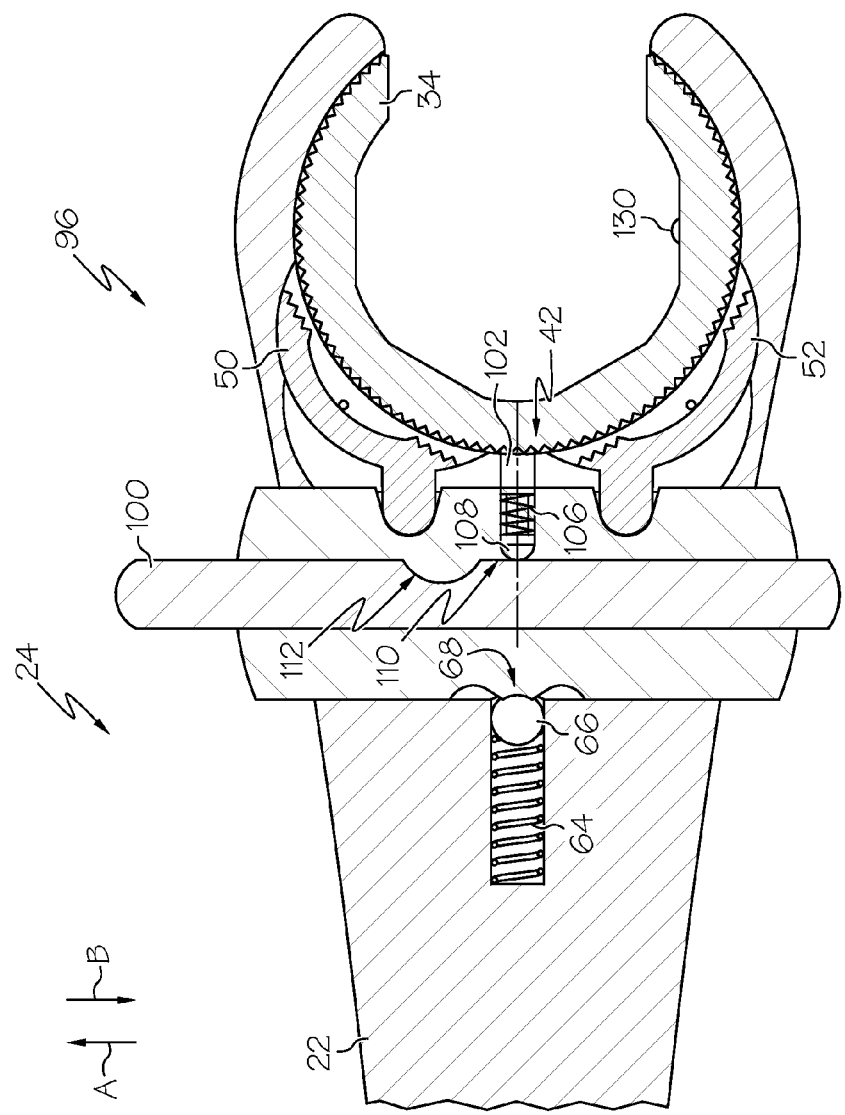
FIG. 7 is similar to FIG. 3, but shows yet another function of the ratchet wrench.

In addition or alternatively, the ratchet wrench 20 can be capable of yet another example function. The selector mechanism can be adapted to perform a fourth function whereby the ratchet member 34 is inhibited, such as prevented, from rotation in any direction and is in a fourth lock position 96. In one example, as shown in FIG. 7, the fourth function can occur by way of a horizontal slider 100 that is slidable, relative to the selector cam 56, in the directions of arrow A and/or B. The horizontal slider 100 can be adapted to function with the selector cam 56 in any of the first, second, or third positions 90, 92, 94. The horizontal slider 100 can cooperate to drive a longitudinally sliding locking pin 102 into engagement with the ratchet member 34 to thereby inhibit rotation thereof. The locking pin 102 can include corresponding teeth for engagement with any of the ratchet teeth 42, or can include other locking structure for engagement with corresponding structure of the ratchet teeth 42. The locking pin can be slidable through another aperture 104 of the recess 28 (see FIG. 2). The locking pin 102 can be resiliently biased, such as by a spring 106, and can be held in place by a retainer 108 in the selector cam 56. The retainer 108 can include a surface, such as a cam surface, adapted to engage with a driving surface 110 of the horizontal slider 100 for pushing the locking pin 102 into engagement with the ratchet member 34. The horizontal slider 100 can also include a recess 112 for receiving the retainer 108 to permit the locking pin 102 to slide towards the left to thereby disengage from the ratchet member 34. The driving surface 110 can be located on either side of the recess 112 such that the locking pin 102 can be engaged with the ratchet member 34 by sliding movement along the direction of arrows A or B, relative to the recess 112. This can permit access to the horizontal slider 100 on one or both sides of the wrench 20. The locking pin 102 can then be released from the ratchet member 34 upon sliding movement in the opposite direction until the retainer 108 is received in the recess 112 again.

Figure 8:
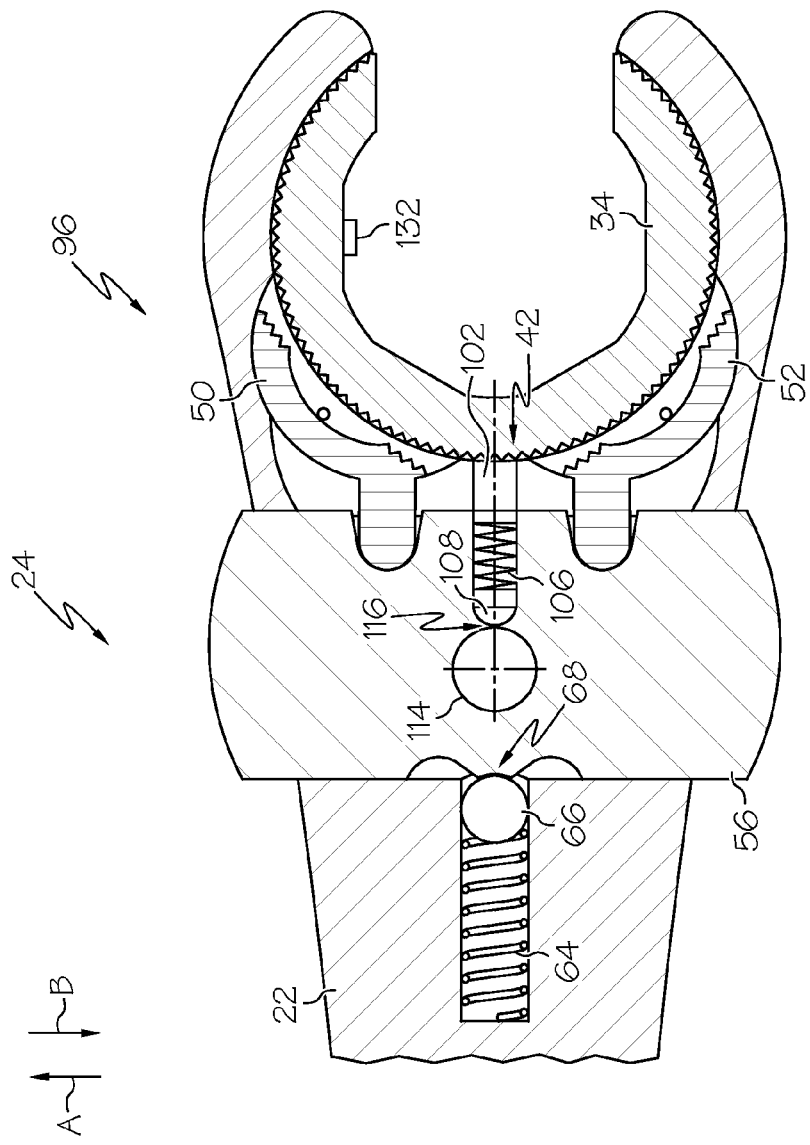
FIG. 8 is similar to FIG. 7, but shows an alternative mechanism of the ratchet wrench.

In another example, as shown in FIG. 8, the fourth function can occur by way of a vertical slider 114 that is slidable, relative to the selector cam 56, in a vertical or angled direction. For example, the vertical slider 114 can be slidable generally into and out of the plane of the page of FIG. 8 (i.e., generally perpendicular to the directions of arrow A and/or B). The vertical slider 114 can be function generally similarly to the horizontal slider 100, though with movement in the vertical plane to achieve the fourth lock position 96. The vertical slider 114 can also be adapted to function with the selector cam 56 in any of the first, second, or third positions 90, 92, 94. As before, the vertical slider 114 can cooperate to drive the longitudinally sliding locking pin 102 into engagement with the ratchet member 34 to thereby inhibit rotation thereof. The locking pin 102 can include corresponding teeth for engagement with any of the ratchet teeth 42, or can include other locking structure for engagement with corresponding structure of the ratchet teeth 42. The locking pin can be slidable through another aperture 104 of the recess 28 (see FIG. 2). The locking pin 102 can be resiliently biased, such as by the spring 106, and can be held in place by the retainer 108 in the selector cam 56. The retainer 108 can include a surface, such as a cam surface, adapted to engage with a driving surface 116 of the horizontal slider 100 for pushing the locking pin 102 into engagement with the ratchet member 34. The vertical slider 114 can also include a recess (not shown) for receiving the retainer 108 to permit the locking pin 102 to slide towards the left to thereby disengage from the ratchet member 34. The driving surface 116 can be located on one side, or both sides, of the recess 112 such that the locking pin 102 can be engaged with the ratchet member 34 by vertical sliding movement along into and/or out of the plate of the page, relative to the recess. This can permit access to the vertical slider 114 on one or both sides of the wrench 20. The locking pin 102 can then be released from the ratchet member 34 upon sliding movement in the opposite direction until the retainer 108 is received in the recess again.

In addition or alternatively, the vertical slider 114 can include an enlarged cam (not shown), such as a ramped or wedge surface, adapted to drive the retainer 108 and locking pin 102 towards the right in FIG. 8 upon pressing the vertical slider 114 vertically downwards toward the wrench handle 22. The enlarged cam can be adapted for vertical sliding movement of the vertical slider 114 into and/or out of the plate of the page. In addition or alternatively, the vertical slider 114 can be replaced by a vertically oriented, rotatable cam system disposed generally about the top surface of the wrench handle 22 (e.g., such as near or through the selector cam 56). In addition or alternatively, the horizontal slider 100 of FIG. 7 and the vertical slider 114 of FIG. 8 may be independent from and permit the pawls 50, 52 to remain in a desired position, such as any of those shown in FIGS. 3-5.

Figure 9:
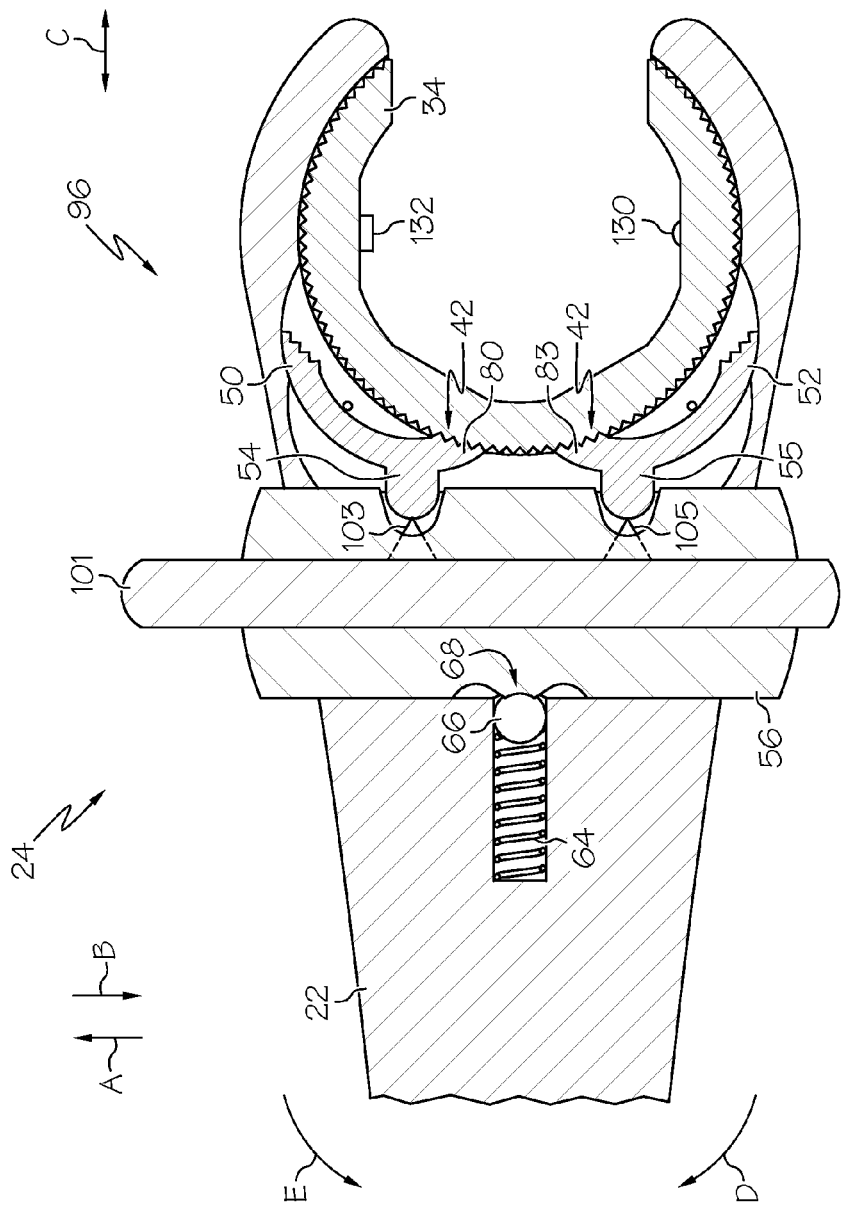
FIG. 9 is similar to FIG. 7, but shows another alternative mechanism of the ratchet wrench.

In addition or alternatively, as shown in FIG. 9, the fourth function can occur when the pawls 50, 52 are shifted to achieve the fourth lock position 96. For example, one of the pawls 50 can be pivoted such that one plurality of pawl teeth 80 engage the teeth 42 of the ratchet member 34, while the other of the pawls 52 is pivoted in the opposite direction such that another plurality of pawl teeth 83 engage the teeth 42 of the ratchet member 34. Thus, the ratchet member 34 is in the lock position and is inhibited, such as prevented, from rotating in the direction of either arrows D or E. For example, attempting to rotate the handle 22 in the direction of arrow D will impinge or bind the pawl 50 as discussed herein to inhibit rotation in said direction, while attempting to rotate the handle 22 in the direction of arrow E will impinge or bind the pawl 52 to also inhibit rotation in said direction.

The ratchet wrench 20 can be shifted to and maintained in the fourth lock position 96 via the pawls 50, 52 in various manners. In one example, a horizontal slider 101 can be provided together with or independent of the selector cam 56. The horizontal slider 101 can be used to actuate the pawl tongues 54, 55 for pivoting the pawls 50, 52 into the lock position 96. In one example, the horizontal slider 101 can include a pair of driving cams 103, 105 that, upon sliding movement of the horizontal slider 101 in either of the directions of arrows A or B, can drive the pawl tongues 54, 55 towards the right in along the direction of arrow C for pivoting the pawls 50, 52 to the lock position 96. Thereafter, sliding movement of the horizontal slider 101 in the opposite direction will release the driving cams 103, 105 from the tongues 54, 55 to permit the pawls 50, 52 to be released to the neutral position. Still, the horizontal slider 101 could be replaced by a vertical slider (not shown) or rotatable cam system disposed generally about the top surface of the wrench handle 22 (e.g., such as near or through the selector cam 56) and can be pressed downwards and/or forwardly towards the pawls 50, 52. A cam, such as a ramped or wedge surface, can drive the pawl tongues 54, 55 towards the right in along the direction of arrow C for pivoting the pawls 50, 52 to the lock position 96. The lock mechanism can be resiliently maintained in the engaged and/or dis-engaged positions. It is understood that the locking system of FIG. 9 could also be used together with the locking pin 102 and associated structure described in FIG. 7.

In yet another example, different, such as opposite, portions of the selector cam 56 can be actuated against the pawl tongues 54, 55 to independently pivot each pawl 50, 52 in the different directions. For example, the selector cam 56 can be formed of two independent elements that are independently moveable and are each coupled to one of the pawl tongues 54, 55. That is, different portions of the selector cam 56 can each be pressed inwardly to drive the pawl tongues 54, 55 (e.g., via a ramped or wedge surface, etc.) to pivot the pawls 50, 52 in the different directions.

A separate release mechanism (not shown) can be provided to release any of the various horizontal or vertical sliders (or even the selector cam 56) back to a neutral position to again permit rotation of the ratchet member 34. In one example, a release button (not shown) can be utilized to free the different horizontal or vertical sliders (or even the selector cam 56) back to the neutral position. When the different portions of the selector cam 56 are pressed inwardly, an internal release cam, which can be resiliently biased, can be triggered to hold the different portions of the selector cam 56 in the locked position. The release button can be linearly movable, rotatable, etc. and may be resiliently biased, etc.

Various other features can also be provided. For example, various portions of the wrench 20 can include alignment indicia 111, such as one or more lines, that can visually indicate when the ratchet member 34 is oriented at a desired rotational position. For example, each of the ratchet member 34 and the handle 22 can include a line that, when in alignment, indicates that an open end (i.e., the gap 40) of the ratchet member 34 corresponds to an open end (i.e., the gap 26) of the head 24. Still other alignment indicators can be used, including mechanical, electrical, analog and/or digital structure, displays, sound, etc.

In addition or alternatively, the ratchet member 34 can be adapted to receive a plurality of interchangeable inserts. A variety of wrench inserts 120A-120G are depicted in FIGS. 10-19. Each of the inserts 120A-120G can have various open-end or closed-end geometries, sizes, and can be adapted to interact with various mechanical fasteners, other tools, etc. The inserts 120A-120G can each have coupling structure to engage with the inner surface 44 of the ratchet member 34 so that any one of the variety of inserts may be operably retained by the ratchet member 34 and used with the ratchet wrench 20. The various inserts can be similar to those described in U.S. Pat. No. 5,388,479 entitled Universal Ratchet Wrench by John Sroka, which is incorporated herein by reference thereto.

In one example, as shown in FIGS. 10-19, the coupling structure of the ratchet member 34 and inserts 120A-120G can include corresponding geometry adapted to retain the interchangeable inserts via a relatively tight fit. For example, the inner surface 44 can have a predetermined, keyed shape and the wrench inserts 120A-120G can have a similar geometry. Such a keyed shape can facilitate correct insertion of the inserts, as well as inhibiting, such as preventing, inadvertent relative rotation between the inserts and the ratchet member 34. The geometry of the outer surface 122 of the inserts can correspond to the inner surface 44 of the ratchet member 34. The corresponding geometry can include various tapers or the like adapted to facilitate retaining the interchangeable inserts. Though one geometry is shown, it is understood that the inner surface 44 and outer surface 122 can also have various other geometries. The inner surface 44 can have at least two, such as three or four, major supporting surfaces for the interchangeable inserts 120A-120G.

In addition or alternatively, the coupling structure can include a keyed structure. In one example, as shown in FIGS. 14-19, the ratchet member 34 can be provided with a spring loaded ball detente 130 and/or a key 132, and the interchangeable inserts can be similarly provided with a round recess 134 and/or a square recess 136 to coact with the key and the ball detente, respectively.

In addition or alternatively, the wrench 20 can be provided with a converting attachment (see FIGS. 14-15), such as insert 120E, that includes a standard square drive shank 140 for use with various sockets. The drive shank 140 may be any of the standard sizes such as a three-eighths inch drive or a one-half inch drive thus enabling the wrench to be used with the standard socket sets widely used by both backyard mechanics and professional mechanics.

In addition or alternatively, as shown in FIG. 1, a double ended wrench 20 can have two open ends. In this embodiment, the ends may be of differing sizes to accommodate differing sized inserts or sockets, thus increasing the number of wrench sizes that may be accommodated by a single handle tool. For example, one end may be configured to handle sockets for bolt sizes five-eighths inch up to one inch (i.e., 15 mm up to 26 mm) and the other end may accommodate sizes one-quarter of an inch up to five-eighths of an inch (i.e., 4 mm up to 15 mm), though various other sizes are contemplated. The ratchet mechanism used in the wrench depicted in the drawings could be any one or combinations of the example mechanisms described herein. In another example, not shown, a double ended wrench can have one end with a ratcheting mechanism as described herein (e.g., ratchet member 34, etc.), while the other end of the wrench can be provided as a single size, fixed head wrench. Thus, the ratcheting end of the wrench can be used with the various inserts, while the fixed end can be used as a single sized wrench, such as with relatively larger torque applications or applications that can benefit from using a relatively smaller wrench end size.

Alternatively, though not shown, it is understood that the wrench 20 can include only one operable head 24 provided on a handle 22 with gripping structure or the like. This construction can be beneficial to reducing the overall size of the wrench 20. For example, a relatively smaller version of the wrench may accommodate sizes one-quarter of an inch up to three-eighths of an inch (i.e., 4 mm up to 10 mm), while a relatively larger version of the wrench may accommodate sizes three-eighths of an inch up to five-eighths of an inch (i.e., 9 mm up to 15 mm), while an even relatively larger version of the wrench may accommodate sizes five-eighths of an inch up to one inch (i.e., 15 mm up to 26 mm). It is understood that various sized versions of the wrench can accommodate various other ranges.

It should also be appreciated that in each of the examples described herein the ratchet member 34 may be provided with a fixed bolt-head engaging surface having configurations similar to the surfaces on the insertable sockets depicted. That is, the inner surface 44 of the ratchet member 34 can be provided as a fixed aperture sized for interacting with a particular, fixed-size fastener without the use of an interchangeable insert. Still, an interchangeable insert can still be used therewith for various other sized fasteners. In addition or alternatively, ratchet member 34 can be removable and replaceable, such as for maintenance, wear, and/or alternative sizing. For example, a ratchet member 34 having a relatively larger inner surface 44 for accommodating relatively larger inserts can be removed from the wrench 20 and replaced with another ratchet member 34 having a relatively smaller inner surface 44 for accommodating relatively smaller inserts.

The invention has been described with reference to the example embodiments described above. Modifications and alterations will occur to others upon a reading and understanding of this specification. Examples embodiments incorporating one or more aspects of the invention are intended to include all such modifications and alterations insofar as they come within the scope of the appended claims.

What is claimed is:

1. A ratchet wrench comprising,
   a wrench handle having a head formed with an open end, the open end defining an axis that extends therethrough, the head having a recess formed on an inner surface thereof;
   a ratchet member seated in the recess for rotation about the axis, comprising a radially extending outer surface that is generally parallel to the axis, the surface being provided with a plurality of ratchet teeth;
   a pawl disposed within an aperture of the recess and adapted to pivot relative to an orientation pin, the pawl being provided with a first plurality of pawl teeth spaced a distance from a second plurality of pawl teeth, the first and second pluralities of pawl teeth being disposed for movement into and out of engagement with the ratchet teeth, the pawl further comprising a curved outer surface that rides against a correspondingly curved inner wall of the aperture and is in continuous engagement with the correspondingly curved inner wall;
   a selector mechanism for selectively pivoting the pawl to move a selected one of the first and second pluralities of pawl teeth into engagement with the ratchet teeth, the selector mechanism being at least partially disposed within the wrench; and
   at least two independently operable pawls that each comprise first and second pluralities of pawl teeth being disposed for movement into and out of engagement with the ratchet teeth, wherein the selector mechanism comprises a selector cam, and each pawl comprises a tongue independently engaged with the selector cam such that movement of the selector cam causes pivoting motion of the pawls, and wherein the selector cam is disposed in a second aperture that extends through the head of the wrench and is linearly slidable within the second aperture.

2. The ratchet wrench of claim 1, wherein the selector cam synchronizes the operation of the pawls.

3. The ratchet wrench of claim 1, wherein the selector cam is held in a desired position by a ball resiliently pushing against cam position grooves.

4. The ratchet wrench of claim 1, wherein the selector mechanism is adapted to selectively and independently pivot the first and second pawls to into and out of engagement with the ratchet member to selectively permit the ratchet member to perform at least three functions.

5. The ratchet wrench of claim 4, wherein the at least three functions comprise ratcheting rotation of the ratchet member in only a first direction, ratcheting rotation of the ratchet member in only a second direction opposite the first direction, and free rotation of the ratchet member in either of the first second directions.

6. The ratchet wrench of claim 5, wherein the selector mechanism is adapted to perform a fourth function whereby the ratchet member is inhibited from rotation.

7. The ratchet wrench of claim 1, further comprising torque sensing structure operatively coupled to the ratchet member.

8. The ratchet wrench of claim 1, wherein the recess defines a flange with a flange sidewall, and the ratchet member defines an inset radial bore adapted to slide against the flange sidewall.

9. The ratchet wrench of claim 1, further comprising a plurality of interchangeable inserts operably retainable within the ratchet member and wherein the ratchet member is adapted to retain the interchangeable members therein.

10. A ratchet wrench, comprising:
    a wrench handle having a head formed with an open end, the open end defining an axis that extends therethrough, the head having a recess formed on an inner surface thereof;
    a ratchet member seated in the recess for rotation about the axis, comprising a radially extending outer surface that is generally parallel to the axis, the surface being provided with a plurality of ratchet teeth that extend along a predetermined radial distance of the surface;
    first and second pawls each disposed within respective apertures of the recess and adapted to pivot relative thereto, each of the first and second pawls being provided pawl teeth disposed for selective movement into and out of engagement with the ratchet teeth;
    wherein the plurality of ratchet teeth extend along a predetermined radial distance of the surface of the ratchet member such that the ratchet member is permitted to rotate completely about the axis with at least a portion of the ratchet teeth always in contact with pawl teeth of at least one of the first and second pawls; and
    further comprising a selector mechanism for selectively and independently pivoting the first and second pawls to into and out of engagement with the ratchet member to selectively permit the ratchet member to perform at least three functions,
    wherein the selector mechanism is disposed in another aperture that extends through the head of the wrench and is linearly slidable within the another aperture.

11. The ratchet wrench of claim 10, wherein the open end of the head defines a gap having a width and the ratchet member has an outer diameter, the width of the gap being less than the outer diameter of the ratchet member to a degree sufficient to inhibit the ratchet member from inadvertent removal from the recess of the head.

12. The ratchet wrench of claim 11, wherein the width of the gap is less than the outer diameter of the ratchet member by a ratio of at least 1:4.

13. The ratchet wrench of claim 10, wherein the selector mechanism is adapted to perform a fourth function whereby the ratchet member is inhibited from rotation.

\* \* \* \* \*